United States Patent [19]

Joergensen et al.

[11] Patent Number: 5,371,198

[45] Date of Patent: Dec. 6, 1994

[54] METHOD FOR PROTECTION OF PROTEOLYSIS-SUSCEPTIBLE PROTEIN DURING PROTEIN PRODUCTION IN A FLUID MEDIUM

[75] Inventors: Per L. Joergensen, Copenhagen; Poul E. Pedersen, Soeborg; Joergen Petersen, Alleroed; Torben K. Nielsen, Roskilde; Jan. M. Mikkelsen, Gentofte, all of Denmark

[73] Assignee: Novo Nordisk A/S, Bagsvaerd, Denmark

[21] Appl. No.: 848,507

[22] Filed: Mar. 9, 1992

[51] Int. Cl.$^5$ .................. C07K 3/12; C07K 3/24; C07K 3/28; C07K 13/00
[52] U.S. Cl. ............................ 530/412; 530/413; 530/418; 530/419; 530/420; 530/421; 530/422; 435/220; 435/221; 435/226
[58] Field of Search ........ 530/412, 418, 419, 420–424, 530/425; 435/219, 220, 221, 226, 69.1, 69.2, 222, 223

[56] References Cited

U.S. PATENT DOCUMENTS

| | | | |
|---|---|---|---|
| 4,016,039 | 4/1977 | Schreiber | 195/66 R |
| 4,212,946 | 7/1980 | Noraka et al. | 435/212 |
| 5,019,500 | 5/1991 | Ueda et al. | 435/691 |
| 5,191,063 | 3/1993 | Inouye et al. | 530/324 |

FOREIGN PATENT DOCUMENTS

| | | | |
|---|---|---|---|
| 0201017 | 11/1986 | European Pat. Off. | |
| 0415296 | 3/1991 | European Pat. Off. | 435/222 |
| 8906279 | 7/1989 | WIPO | 435/222 |
| WO90/02175 | 3/1990 | WIPO | |

OTHER PUBLICATIONS

Wells, J. A., et al., 1987, Proceedings of the National Academy of Sciences, U.S.A., 84:1219–1223.
Russell, A. J., et al., 1987, Journal of Molecular Biology, 193:803–813.
Pantoliano, M. W., 1988, Biochemistry, 27:8311–8317.
Meloun, B., et al., 1985, FEBS Letters, 183(2):195–199.
McPhalen, L. A. et al., 1985, FEBS Letters, 188(1):55–58.
Hirono, S., et al., 1984, Journal of Molecular Biology, 178:389–413.
Bode, W., et al., 1986, The EMBO Journal, 5(4):813–818.
Williams et al., Science, vol. 215, pp. 687–689 (1982).
Johnson et al., Kininogenases–kallikrein, pp. 113–118 (1977).
Novikov et al., Biotech. Lett., vol. 12, No. 8, pp. 547–550 (1990).
Kominami et al., Biochem. Biophys. Res. Comm., vol. 144, No. 2, pp. 749–756 (1987).
Connor, Biochem. J., vol. 263, pp. 601–604 (1989).
DeMartino et al., J. Biol. Chem., vol. 261, No. 26, pp. 12047–12052 (1986).
Power et al., Proc. Natl. Acad. Sci. USA, vol. 83, pp. 3096–3100 (1986).
Zhu et al., Nature, vol. 339, pp. 483–484 (1989).
Egnell et al., Gene, vol. 97, pp. 49–54 (1991).
Druckner et al., Arch. Biochem. Biophys., vol. 147, pp. 242–248 (1971).
Van den Burg et al., Biochem. J., vol. 272, pp. 93–97 (1990).
Kim et al., Korean Biochem. J., vol. 23, No. 1, pp. 58–61 (1990).
Coxon et al., Letts. in Appl. Microbiol., vol. 12, pp. 91–94 (1991).

*Primary Examiner*—Robert A. Wax
*Assistant Examiner*—William W. Moore
*Attorney, Agent, or Firm*—Steve T. Zelson; Karen A. Lowney

[57] ABSTRACT

A process for the microbial production of a protein susceptible to inactivation in a fluid production medium by continuously and reversibly protecting said protein against said inactivation during the production stage, separating the protein from the production medium, deprotecting the protein, and recovering the protein product. The process is especially useful for obtaining substantially increased yields of the protein in question by continuously precipitating said protein.

21 Claims, 2 Drawing Sheets

METHOD FOR PROTECTION OF PROTEOLYSIS-SUSCEPTIBLE PROTEIN DURING PROTEIN PRODUCTION IN A FLUID MEDIUM

FIELD OF THE INVENTION

The present invention relates to methods of producing and recovering proteins, and especially recombinant proteins. The methods are particular useful for microbial production and subsequent recovery of the proteins from the growth medium.

BACKGROUND OF THE INVENTION

In production of proteins, especially microbial production, the instability of these proteins during the production process, especially the fermentation process is of major concern to assure the profitability of the production.

When using recombinant techniques for the production of heterologous proteins it has been found that the protein product often forms aggregates which are recognizable within the cell as "inclusion bodies" (Williams et al., Science 215 (1982) 687–689).

With the accumulation of the protein in the cytoplasma or the periplasmatic space either as inclusion bodies or in an otherwise aggregated or complexed state, many proteins have been found to be protected against proteolysis or other modifications in the production organism.

In the fluid production medium protease inhibitors like bovine aprotinin have been added to protect heterologous products like insulin against proteolytic digestion in mammalian culture (.Johnson et al. in Kininogenases-kallikrein 4 eds. Haberland et al. (1977) 113–118, Schattauer-Verlag), and a similar result has been obtained by Novikov et al. (Biotech. Lett. 12 (1990) 547–550) with addition of synthetic serin proteinase inhibitors to the growth medium in a fermentation of a Bacillus subtilis strain expressing proinsulin.

Autoproteolysis has been shown to be a quite common event in biological systems. By use of an inhibitor of cysteine proteinases a higher level of the proteinases cathepsin B, H and C has been found in rats (Kominami et al., Biochem. Biophys. Res. Comm. 144 (1987) 749–756). Connor (Biochem. J. 263 (1989) 601–604) has shown that procathepsin D undergoes autoproteolytic change to produce the mature cathepsin D even at low concentrations (<1 g/ml). In bovine heart the Ca-dependent protease II seems to be activated by autoproteolytic cleavage of a subunit and by further successive cleavages the Ca-dependence of the protease is lowered (Demartino et al., J. Biol. Chem. 261 (1986) 12047–12052).

In microorganisms autoproteolysis was shown to be the most likely cause of the maturation of a subtilisin type protease in Bacillus subtilis during the secretion of the proform (Power et al., PNAS 83 (1986) 3096–3100). Later studies by Zhu et al. (Nature 339 (1989) 483–484) and Egnell and Flock (Gene 97 (1991) 49–54) have shown that the proform functions to guide the subtilisin into the right conformation in order to achieve an autoproteolytic maturation.

With purified proteases autodigestion is a common cause of inactivation of the enzyme. Drückner and Botchers (Arch. Biochem. Biophys. 147 (1971) 242–248) have described the limited autodigestion of thermolysin from *Bacillus stearothermophilus* at high temperature and low calcium concentration. Van den Burg et al. (Biochem. J. 272 (1990) 93–97) have examined the autocatalytic degradation of a neutral protease from Bacillus subtilis and Kim et al. (Han'guk Saenghwa Hakhoechi 23 (1990) 58–61) have identified the major cleaving sites of subtilisin Carlsberg. Autoproteolysis might be a limiting factor in obtaining high fermentation yields of proteases.

During fermentations the problems concerning the proteolytic degradation of the products are traditionally minimized in adjusting the growth conditions such as temperature, pH and the amount of available nitrogen source or addition of protease inhibitors (International Patent Application No. PCT/DK 89/00194), but still the proteolytic degradation of the product very often will set the limitations for the yield.

On the other hand Coxon et al. (Letters in Appl. Microbiol. 12 (1991) 91–94) find that the use of a *Bacillus subtilis* strain deficient in extracellular proteases shows increased tendency to cell lysis as the cells approach stationary growth phase.

Therefore methods to minimize the contact between the product and the rest of the growth medium, especially proteases, during fermentation will be a valuable tool in process optimization. This will make it possible to use fermentation conditions which increase the productivity of the protein where it has no influence if more protease is produced. The use of a minimal medium gives better product quality as a major advantage, since it will result in an improved recovery process. However, the yield of protease is often rather low, which to a certain extent is ascribable to an increased tendency for autoproteolytic cleavage of the protease.

In this specification and the claims protein variants to be used or contemplated to be used in the present invention are described using the following nomenclatures for ease of reference:

Original amino acid(s) position(s) substituted amino acid(s)

According to this the substitution of Glutamic acid for glycine in position 195 is designated as:

Gly 195 Glu or G195E a deletion of glycine in the same position is:

Gly 195 * or G195* and insertion of an additional amino acid residue such as lysine is:

Gly 195 GlyLys or G195GK

Where a deletion is indicated an insertion in such a position is indicated as:

* 36 Asp or *36D for insertion of an aspartic acid in position 36

Multiple variants are separated by pluses, i.e.:

Arg 170 Tyr+Gly 195 Glu or R170Y+G195E representing a multiple variant "mutated" in positions 170 and 195 substituting tyrosine and glutamic acid for arginine and glycine, respectively.

SUMMARY OF THE INVENTION

Consequently it is the object of the present invention to provide for a novel process for the production of proteins, especially produced through recombinant methods. Through the process of the invention it is made possible to obtain greatly enhanced yields of the proteins of interest in comparison with known processes due to the increased stability in the growth medium.

This object is achieved through a process for the microbial production of a protein susceptible to inactivation in a fluid production medium by continuously and reversibly protecting said protein against said inactivation during the production stage, separating the protein from the production medium, deprotecting the protein, and recovering the protein product.

BRIEF DESCRIPTION OF THE DRAWING

In the following the invention is described in detail with the reference to the drawing, wherein.

DETAILED DESCRIPTION OF THE INVENTION

Figure 1A:
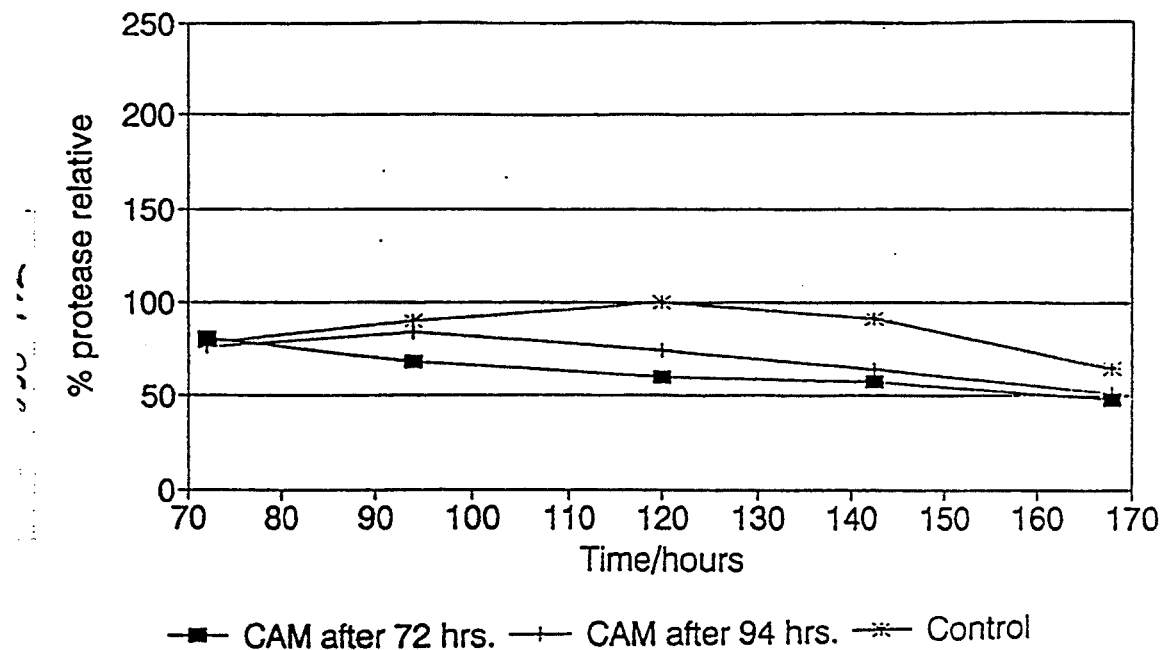
FIGS. 1a and FIG. 1b show yields for a process according to the invention compared to the prior art in a complex growth medium.

According to the invention there is provided a process for the production of a protein susceptible to inactivation or degradation in a fluid production medium by continuously and reversibly protecting said protein against said inactivation or degradation during the production stage, separating the protein from the production medium, deprotecting the protein, and recovering the protein product.

According to the invention the protein of interest is protected during fermentation. Ibis protection is contemplated to be interpreted broadly covering a number of possible methods of which removal of the protein from the medium through precipitation by addition of a precipitating agent is one, and removal by extraction into another phase, where the protease responsible for the degradation of the protein is not likely to follow is another.

A further solution will be to change the solubility of the protein in the fermentation medium. A way to do this is to implement mutations in the protein by genetic engineering to reduce its solubility.

A still further solution is to use aggregation by help of another protein e.g. an inhibitor or an antibody, which can be removed reversibly.

In a preferred embodiment of the invention said protection is performed by removing said protein from the product and especially by precipitation.

The precipitation may be obtained through the addition of a precipitating agent to the production medium, which addition may be performed by batchwise addition or, as preferred, by continuously adding the precipitating agent to the production medium.

The precipitating agent may be a salt, such as one selected from the Group I metal salts, the Group II metal salts, the corresponding ammonium salts of the Group I or II metal salts, or mixtures thereof, preferably a salt where the valency of the anion of the salt is divalent or higher, preferred salts are the phosphate, sulfate, and citrate salts, especially preferred salts are sodium phosphate, ammonium phosphate, sodium citrate, sodium sulfate and ammonium sulfate or the corresponding potassium and cesium salts, sulfate salts are most desirable. However, certain halogenide salts and acetates are also applicable, especially the chloride salts.

In another embodiment the precipitating agent is a low molecular weight organic solvent, such as methyl ethyl ketone, acetone, methanol, ethanol, 1-propanol, isopropanol, tert-butanol, n-butanol, dimethyl formamide, dimethyl sulfoxide, monoethyl ether of ethylene glycol, monomethyl ether of ethyl glycol, and the like.

In the above embodiments a precipitation agent, such as a salt or a low molecular weight organic solvent is added to the protein producing medium during fermentation. Addition of the precipitation agent causes the protein and/or protein complex to precipitate, and a "slurry" or "cake" is produced. Throughout the description and claims, the term "cake" may be used interchangeably with the term "slurry", and it is intended to include those instances where the "cake" is so wet that it would be considered a "slurry". The cake containing the protein or protein complex is separated from the remaining solution either continuously or when the fermentation has been terminated. Usually this separation is achieved by filtration and the filtrate containing impurities may be considered waste. If there is still excess mother liquor in the cake, it can be substantially removed from the slurry or cake by employing any of several methods. For instance, the excess mother liquor may be removed by additional filtration, such as by a pressure differential (e.g. suction filtration); gravity sedimentation; or centrifugation. The removal may be followed by a water wash and air blowing, providing a relatively drier cake.

The precipitation agents employed in the present invention are innocuous. By the term "innocuous" it is intended to mean that the precipitation agents contemplated by this invention (1) do not destroy the protein of interest, (2) do not negatively influence the end use of the protein product, and (3) do not require extensive additional processing to remove. In some instances it is even unnecessary that the protein product be free of the precipitation agent. The precipitation agents contemplated by the present invention are broadly useful for many proteins.

It is preferred to employ a salt as the precipitation agent in the present invention, but low molecular weight organic solvents will work well too as long as they are compatible with the particular polyol later employed for solubilizing the protein. Preferred organic solvent precipitation agents are methyl ethyl ketone, acetone, methanol, ethanol, 1-propanol, isopropanol, tert-butanol, n-butanol, dimethyl formamide, dimethyl sulfoxide, monoethyl ether of ethylene glycol, monomethyl ether of ethyl glycol, and the like.

Organic solvent precipitation agents may be added to the medium containing the protein in a volume amount of 2 to 3 times the volume of the protein-containing solution, care being taken not to poison the cells producing the protein of interest.

If a salt is used as the precipitation agent, it should be selected from the Group I metal salts, the Group II metal salts, the corresponding ammonium salts of the Group I or II metal salts, or mixtures thereof. It is preferred that the valency of the anion of the salt be divalent or higher. Preferred are the phosphate, sulfate, and citrate salts. The especially preferred salts are sodium phosphate, ammonium phosphate, sodium citrate, sodium sulfate and ammonium sulfate. Potassium and cesium salts may also be employed, but of course these are more expensive. Sulfate salts are most desirable. Salt precipitation agents may simply be added to the solution containing the protein, in the amount of 5–50% weight/volume of salt agent to protein-containing solution. More preferably, the salt agent is added in the amount of 12–25% weight/volume. Also, the salt agent may be dissolved in water and the aqueous solution added. As above the addition of the precipitation agent must be performed with care not to poison the protein producing cells or microorganisms.

In a further embodiment the precipitation is performed by performing the production stage under conditions of pH and or ionic strength of the production medium where said protein precipitates from the production medium.

In an especially preferred embodiment of the invention the precipitation is performed by modifying said protein through genetic engineering of the gene coding for said protein, whereby said protein by itself precipitates when entering the production medium.

For the above embodiments of the invention the said separation and deprotection of the protein is usually performed by filtration and subsequent wash of the precipitate with water to remove impurities, extraction/resolubilisation of said protein from the precipitate, and separation of the protein containing extract/solution from the remaining solids.

In one advantageous embodiment of the invention the extraction/resolubilisation is performed by use of a polyol, such as low molecular weight polyethylene glycol and the $C_2$ through $C_8$ alcohols having at least two OH groups, preferably with only two OH groups, especially preferred are polyols where two OH groups are present on adjacent carbon atoms in the chain, and the $C_2$–$C_8$ alcohol is aliphatic and are a straight carbon chain.

In the above embodiment it is especially useful to choose said polyol from the group comprising ethylene glycol, propylene glycol, glycerol, the low molecular weight (about 900 or less) polyethylene glycols, and mixtures thereof.

Next, a polyol solvent, which is mono-propylene glycol (MPG) in the preferred embodiment, is circulated through the cake in order to solubilize and recover the protein and/or protein complex from the cake. It is intended here that the term "to solubilize" means the same thing as the term "to dissolve" or "to extract" and the terms may be used interchangeably. Also, the term "polyol solvent" as used here is intended to mean 100% polyol, essentially 100% polyol, or a polyol-containing solution wherein the polyol is in combination with a compatible co-solvent.

The polyols contemplated in this invention comprise low molecular weight polyethylene glycol and the $C_2$ through $C_8$ alcohols having at least two OH groups. $C_2$–$C_8$ alcohols with more than two OH groups, such as glycerol, may be employed, but it is preferred that there be present only two OH groups. It is especially desirable that these two OH groups be present on adjacent carbon atoms in the chain, and that the $C_2$–$C_8$ alcohol be aliphatic and have a straight carbon chain. Suitable polyols include, for example, ethylene glycol, propylene glycol, mono-propylene glycol, glycerol, the low molecular weight (about 900 or less) polyethylene glycols, and mixtures thereof.

The polyol may be in solution with a co-solvent for the protein, said co-solvent being compatible with the polyol. The co-solvent of course may be water but also may be selected from organic solvents such as acetone, methyl ethyl ketone, methanol, ethanol, 1-propanol, isopropanol, tert-butanol, dimethyl formamide, dimethyl sulfoxide, monomethyl ether of ethylene glycol, monoethyl ether of ethylene glycol, and the like. If the polyol is used in solution with a co-solvent, it is preferred that the polyol be present in an amount of at least 20% by volume, and more preferably 50%. Higher concentrations of polyol, up to 100% polyol with no co-solvent, may also be advantageously employed. Also, the amount of co-solvent may depend on the co-solvent used. For instance, ethanol may also be used as a precipitation agent, i.e. in step (a) of the Summary of Invention mentioned supra. Thus, too much ethanol as a co-solvent with the polyol may cause precipitation rather than solubilization of the protein.

The polyol solvent may be circulated through the protein-containing cake once, but preferably it is recirculated through the cake at least twice to enhance extraction of the protein. It is particularly desirable to employ at least 5 recirculations, and up to as many as 100, or more recirculations may be advantageously employed. The result is a liquid protein product, which is a polyol solution of the protein or protein complex. If a salt precipitation agent has been used, the resultant polyol solution of the protein or protein complex may be cooled to a temperature in a range between room temperature and the freezing point of this solution to cause excess salt to precipitate. In a preferred embodiment with alkaline protease, the cooling is down to approximately 16° C.

Depending on the desired end use, the polyol solution of the protein or protein complex may be used as is, as a liquid protein product, or the solvent may be substantially removed so that the protein by itself may be used. Removal of the solvent may be achieved by one or more known techniques or combinations thereof, thereby providing a substantially solvent-free protein product. One such technique is ultrafiltration, and another is reprecipitation of the protein followed by filtration and/or centrifugation to remove liquid.

Depending on the protein, adjusting the pH toward the acid range during recirculation or reslurrying may enhance extraction. A minor amount of an acid such as acetic, sulfuric or hydrochloric may be advantageously employed for pH adjustment.

Any polyol extract may be formulated, if desired. A preferred method involves extraction with propylene glycol as the polyol solvent and then formulating the PG extract by diluting it with a co-solvent such as diluting it with water to 30% volume PG extract and 70% volume $H_2O$. Any of the other co-solvents mentioned above may also be employed in formulating the extract. The reason for formulating is to cut the protein activity down to whatever is desired depending on the end use of the liquid protein product. Care must be taken not to use too much co-solvent during the formulation or the protein may precipitate instead of remaining in solution.

In another embodiment the removal of the protein from the production medium is performed by transfer of the protein to another fluid medium.

In a yet further embodiment of the invention said protection is performed by forming a complex between the protein of interest and at least one counterpart. In this embodiment it is further preferred that said counterpart is co-expressed with said protein, meaning that the counterpart either naturally is expressed by the host expressing the protein of interest, or that the host through protein engineering has been modified to produce one or both of the complex forming counterparts.

According to the above embodiment said counterpart preferably is an inhibitor for the protein or an antibody to the protein.

In connection with the subtilisin proteases mentioned below it is in this embodiment preferred to use a protease inhibitor, such as the CI-1, CI-2, PSI, Eglin C, Eglin B, TSI-1, SSI, or VSI inhibitor, variants thereof, or a mixture of any of these to protect the subtilisin protease.

In the above embodiment the de-protection of the protein in question, such as a protease, is usually performed through the dissolution of the complex when using the protease in e.g. a detergent composition that is dissolved when making up the wash liquor.

In general, the present invention will work with any extracellularly produced protein provided by fermentation in a nutrient growth medium of protein secreting procaryotic or eucaryotic cells, such as plant or animal cells or microorganisms, such as bacteria, yeast, or fungi. The invention works especially well with enzymes selected from proteases, amylases, amyloglucosidases, lipases, oxido reductases, and oxidases. In the preferred embodiment, the fermentation product, alkaline protease, is employed, which is useful in several industries, particularly the detergent industry.

As especially preferred alkaline proteases subtilisin proteases may be mentioned, especially those listed below:

subtilisin 309, subtilisin 309 modified in at least position 36 or 136, and subtilisin 309 modified as indicated here:
*36D, *36D+R170Y+G195E+K251E,
*36D+H120D+R170Y+G195E+K235L,
*36D+H120D+R170Y+G1-
  95E+K235L+K251E,
*36D+H120D+G195E+K235L, *36D+N76D,
*36D+N76D+H120D+G195E+K235L, *36Q,
*36D+Q59E+N76-
  D+A98R+S99D+H120D+N140D+S141R+-
  R170Y+G195E+K235L+N248D+T2-
  55E+S256K+S259D+A272R,
*36D+Q59E+N76-
  D+A98R+S99D+H120D+N140D+S141R+-
  S156E+A158-
  R+A172D+N173K+K235L+N248D+T2-
  55E+S256K+S259D+A272R.

The following examples illustrate some preferred embodiments of the present invention, and are not intended to limit the claims to the embodiments disclosed in the examples.

EXAMPLES

Comments

By the method of the invention it has been found that it is possible to obtain yields of enzyme of from 100% to 200% and even up to 400% or more of the yield typically obtained by traditional methods.

By utilizing the low solubility in water and high solubility in an organic solvent like monopropylene glycol (MPG) of a protein that is protected through precipitation, it is possible just by using typical enzyme recovery equipment, to produce high quality liquid formulations containing from 2% to more than 10% protein with an enzyme purity of more than 90%.

The recovery process is divided into three phases:

i) washing of the enzyme containing sludge phase.
ii) extraction/resolubilization of the enzyme.
iii) concentration and standardization.

i) The sludge phase which contains approx. 90% of the total enzyme amount, is collected and thoroughly washed with water. All water soluble impurities e.g. color, polysaccharide proteins are removed without any significant loss of enzyme.

ii) The following extraction of the enzyme from the sludge phase with MPG, results in a light extract containing almost only one polymer component—the enzyme.

Because the solubility of such a protein in a water-MPG system is positively correlated with the MPG concentration, and minimum consumption of MPG is a must, it is important to dose the MPG in such a way, that all the precipitated enzyme is redissolved in a system just below the saturation point.

The total extraction yield is typical 90% or more and the volume of MPG used for the extraction corresponds to approx. 40% of the culture broth volume.

iii) The final concentration is typically carried out in two steps: (1) ultrafiltration and (b) evaporation.
  (a) The ultrafiltration process makes it possible to increase the concentration of the enzyme (with fixed MPG-water composition) to a relatively high level without recrystallization/reprecipitation. The concentration level is primarily controlled by the MPG/enzyme level in the final product.

The MPG in the permeate contain very low levels of impurities and can therefore after an evaporation (to 70%-75% MPG) without problems be reused in the extraction step.
  (b) The final standardization is achieved by a simple evaporation and the purity of the product is typically above 90%.

EXAMPLE 1

Complex Growth Medium

A subtilisin 309 protease variant constructed as described in WO 89/06279 and WO 91/00345 and comprising the following modifications: *36D+N76D+H120D+G195E+K235L (S035) was produced by a Bacillus strain transformed to produce said variant fermented in parallel with a Bacillus strain producing the wild type subtilisin 309 protease.

The S035 variant precipitates continuously from the production medium during fermentation and the improved stability of the precipitated protease is shown by incubation of the fermentation media after the protein synthesis was stopped by adding Chloramphenicol (CAM) to the culture.

The productions were performed at 30° C. on a rotary shaking table (300 r.p.m.) in 500 ml baffled Erlenmeyer flasks containing 100 ml protease production medium of the following composition (per liter):

| | |
|---|---|
| Potato starch | 100 g |
| Ground barley | 50 g |
| Soybean flour | 20 g |
| $Na_2HPO_4 \times 12\ H_2O$ | 9 g |
| Pluronic | 0.1 g |
| Sodium caseinate | 10 g |

The starch in the medium is liquified with α-amylase and the medium is sterilized by heating at 120° C. for 45 minutes. After sterilization the pH of the medium is adjusted to 9 by addition of NaHCO$_3$ to 0.1M.

Figure 1B:
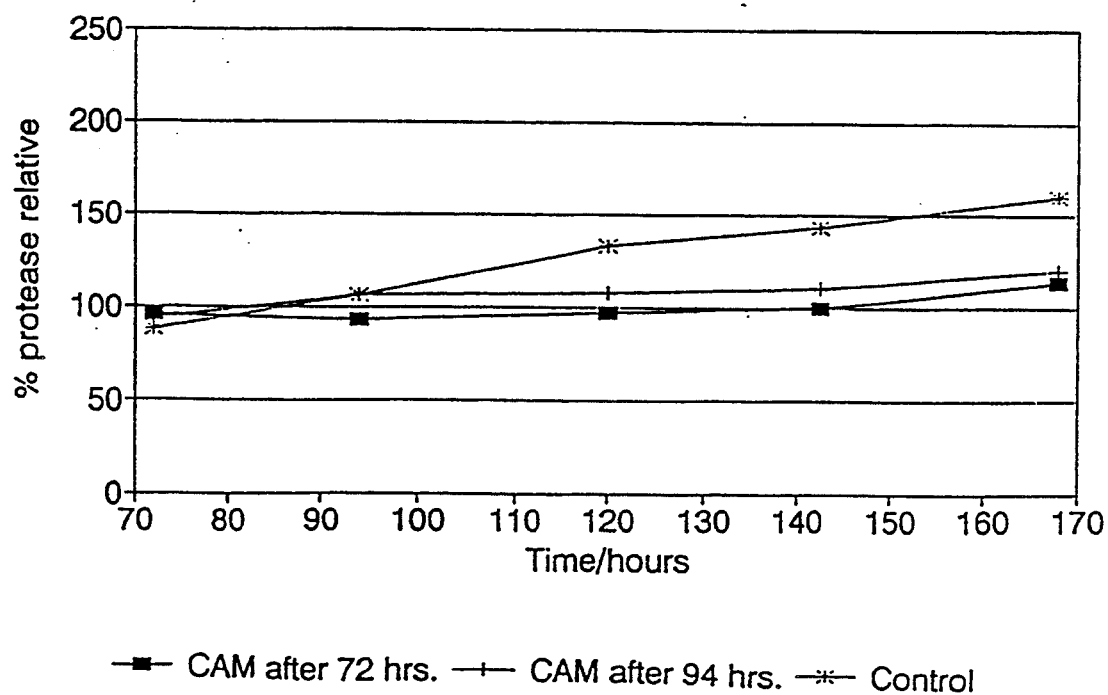

The wild type producing strain for subtilisin 309 was fermented in parallel with the S035 mutant strain. The setup was 2×3 shake flasks of each strain. After 74 hours of cultivation 200 μg/ml CAM were added to the first of the 3 shake flasks (A). After another 20 hours at 94 hours 200 μg/ml CAM were added to the second bottle (B). The third bottle (C) was run parallel without CAM addition. The cultivation was continued and stopped after 168 hours. FIGS. 1a and 1b show the protease level after different periods of incubation. The highest protease level of the normal subtilisin 309 reference strain (C) is set to 100 per cent.

The protease level was detected as described in AF 220/1-GB (a publication available from NOVO NORDISK A/S, Bagsvard, DENMARK).

The results from the fermentation of the wild type subtilisin 309 are shown in FIG. 1a and corresponding for the S035 variant in FIG. 1b, where the protease yield as function of time is indicated.

The increasing level of protease after addition of CAM is probably caused by evaporation from the shake flasks.

The protease level of the S035 variant was assayed after the precipitated enzyme was redissolved in 75 per cent mono-propylene glycol (MPG). The protease level in the supernatant before the resuspension was from 15 to 20 per cent.

EXAMPLE 2

Minimal Growth Medium

Usually cheap complex sources of protein and carbohydrate like ground barley, soy bean meal, cotton seed meal and starch from corn or wheat are used in fermentations of enzymes (Atkinson and Mavituna, 1983, Biochemical Engineering and Biotechnology Handbook, The Nature Press, p. 998-1015). The content of insolubles like non-degradable proteins and carbohydrates and phytate complexes is rather high in these substrates. This gives some restraints in the recovery process especially as regards the solubilization of the precipitated protein. This might be circumvented by fermentation in a minimal salt medium.

In this example the two strains from Example 1 were grown in 2.5 l jar fermenters (MBR mini) at 36° C. with pH controlled at 8.0 by addition of 5N NaOH, vigorous agitation and an aeration of 1.5 vvm. The composition of the growth medium was as follows (in g/L):

| Maltodextrin (Glucidex 6) | 40 |
|---|---|
| Yeast extract | 1 |
| KH$_2$PO$_4$ | 4 |
| KOH | 0.5 |
| NaCl | 0.6 |
| citric acid H$_2$O | 6 |
| CaCl$_2$, 2H$_2$O | 0.8 |
| MgSO$_4$, 7H$_2$O | 4 |
| Pluronic (antifoam agent) | 0.4 |
| Trace metal solution* | 7 |
| Vitamin solution** | 4 |

*Composition: (in g/L): H$_3$BO$_4$ 0.82; MnCl$_2$, 4H$_2$O 0.58; FeCl$_3$, 6H$_2$O 1.95; CuSO$_4$, 5H$_2$O 0.2; BaCl$_2$ 0.1; ZnCl$_2$ 0.2; (NH$_4$)$_6$Mo$_7$O$_{24}$, 4H$_2$O 0.1; CoCl$_2$, 6H$_2$O 0.3; citric acid, H$_2$O 10.
**Composition: thiamin, HCl 150 mg/L and biotin 5 mg/L.

From 24 hours and in the rest of the fermentation two dosage media containing sucrose 60% (w/v) and (NH$_4$)$_2$SO$_4$ 12% (w/v) were fed at a rate of about 4 and 2-2.5 g/L/h respectively.

Figure 2A:
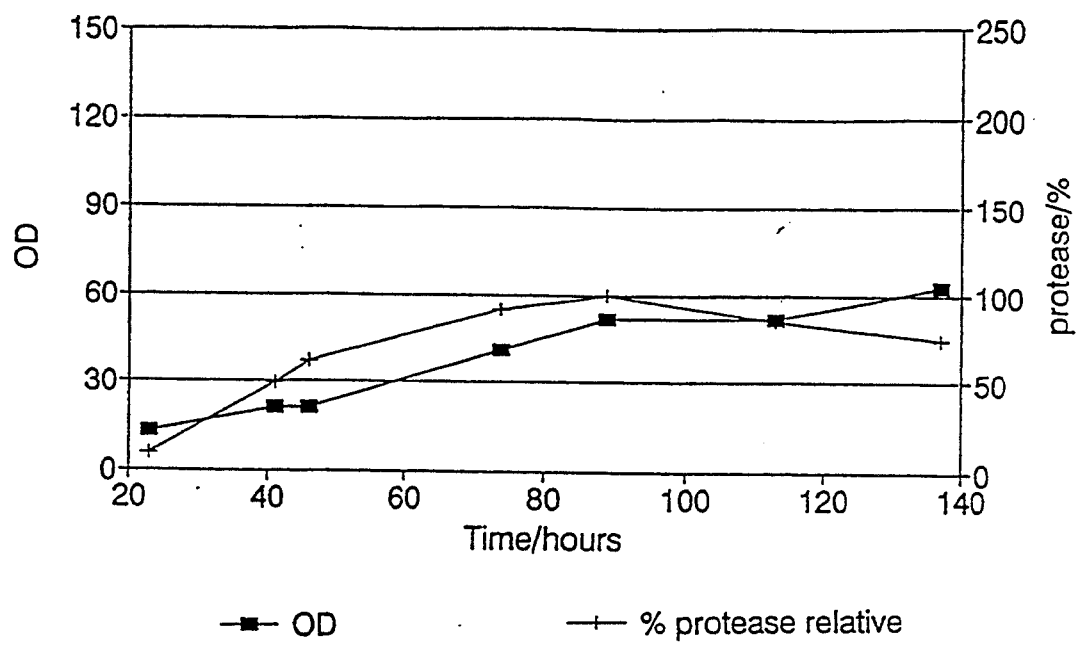
FIGS. 2a and 2b show the same type of results in a minimal growth medium.
Figure 2B:
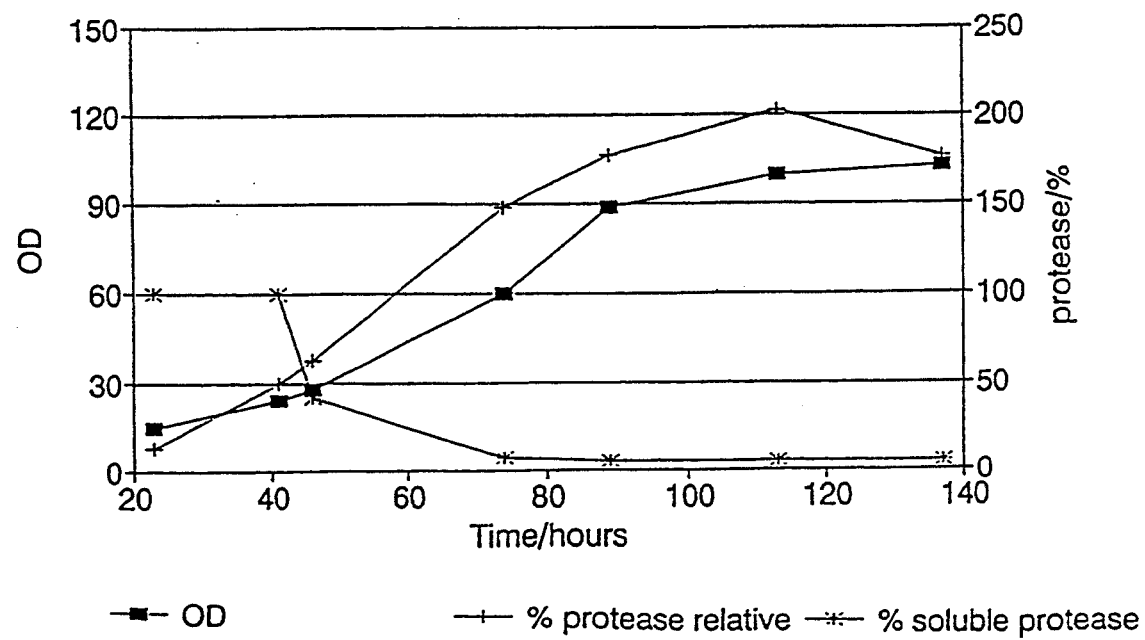

The growth curves (shown as OD$_{650nm}$) and the curves of protease concentrations (in % of the highest concentration obtained with the wild type producing strain) are shown in FIGS. 2a and 2b for the wild type and S035 variant, respectively.

Protease content was determined according to AF 220/1GD. In addition for S035 the fraction of protease in solution is shown as % of total protease concentration. The remarkably higher expression of S035 (FIG. 2b) as compared to subtilisin 309 (FIG. 2a) shows an even greater advantage of the precipitation during fermentation with a minimal growth medium than with a complex growth medium. The very low fraction of soluble S035 in the minimal medium must be a major explanation to this difference in protease concentration. Without the precipitation the use of a minimal medium is no alternative to complex medium.

As an advantage of the following purification of the precipitated protease the volume of the insoluble matter is only about half the size as compared to a fermentation with a complex growth medium with the same cell mass.

EXAMPLE 3

Purification

The culture broth was pretreated with calcium chloride and water (per. kg culture broth: 25 g CaCl$_2$x2H$_2$O and 1 l water) and the pH was adjusted to 8.0 with caustic soda. The suspension was then flocculated by adding cationic and anionic flocculants (per. kg culture broth: 8 g Superfloc C 521 and 250 mg Superfloc A 130, respectively).

The enzyme containing sludge phase was separated from the clear supernatant by centrifugation and was then washed twice at pH 5.5 with water containing 4% w/w CaCl$_2$.

The sludge containing the precipitated enzyme was then mixed thoroughly with mono-propylene glycol (MPG) at pH 7.5 and room temperature (20° C. to 25° C.) for about one hour. MPG used for the resolubilization corresponds to approx. 1.1 times the weight of the sludge- The MPG-water extract was separated from the sludge by centrifugation.

The remaining soluble enzyme in the sludge was washed out with tap water and the suspension was centrifuged. The MPG and water extracts were combined, filtered and ultrafiltrated. The ultrafiltration was carried out at pH 5.5-6.0 and at an increasing temperature (proportional to the concentration factor) from 5° C. to 25° C. When an enzyme-MPG level corresponding to approx. 3.5 g enzyme/100 g MPG was achieved, the ultrafiltration was stopped and the final standardization was carried out by evaporation. The final product contained typically 65% MPG and 2.3% enzyme.

We claim:

1. A process for the microbial production of a protein susceptible to proteolytic inactivation or degradation in a fluid production medium comprising continuously and reversibly protecting said protein against said inactivation or degradation during the production stage, separating the protein from the production medium, deprotecting the protein, and recovering the protein, wherein reversible protection is performed by precipitation of the protein from the production medium by continuous addition of a precipitating agent to the production medium and wherein the production stage is performed under conditions of pH and/or ionic strength where said protein precipitates from the production medium.

2. The process according to claim 1, wherein said precipitating agent is a salt, selected from the group consisting of the Group I metal salts, the Group II metal salts, the corresponding ammonium salts of the Group I or II metal salts, and mixtures thereof.

3. The process according to claim 2 wherein the valency of the anion of the salt is divalent or higher.

4. The process according to claim 3 wherein the salt is a phosphate, sulfate or citrate salt.

5. The process according to claim 4 wherein the salt is selected from the group consisting of sodium phosphate, ammonium phosphate, sodium citrate, sodium sulfate, ammonium sulfate, and the corresponding potassium and cesium salts.

6. The process according to claim 1, wherein said precipitating agent is a low molecular weight organic solvent, selected from the group consisting of methyl ethyl ketone, acetone, methanol, ethanol, 1-propanol, isopropanol, tert-butanol, n-butanol, dimethyl formamide, dimethyl sulfoxide, monoethyl ether of ethylene glycol and monomethyl ether of ethyl glycol.

7. The process according to claim 1, wherein said precipitation is performed by performing the production stage under conditions of pH and or ionic strength of the production medium where said protein precipitates from the production medium.

8. The process according to any one of claims 2–7, wherein said separation and deprotection of the protein is performed by filtration, centrifugation, gravity thickening, hydro cyclone separation, flocculation, or flotation, and subsequent wash of the precipitate with water to remove impurities, extraction/resolubilisation of said protein form the precipitate, and separation of the protein containing extract/solution from the remaining solids.

9. The process of claim 8 wherein the separation and deprotection is performed by filtration or centrifugation.

10. The process according claim 8, wherein said extraction/resolubilisation is performed by use of a polyol.

11. The process according to claim 10, wherein said polyol is chosen from ethylene glycol, propylene glycol, monopropylene glycol, glycerol, polyethylene glycols, and mixtures thereof.

12. The process according to claim 10 wherein the polyol is selected from the group consisting of low molecular weight polyethylene glycol and $C_2$–$C_8$ alcohols having at least two OH groups.

13. The process according to claim 10 wherein the polyol has two OH groups present on adjacent carbon atoms, and the $C_2$–$C_8$ alcohol is aliphatic and has a straight carbon chain.

14. The process according to claim 1, wherein said protein is an enzyme selected from the group consisting of an oxidoreductase, transferase, hydrolase, lyase, isomerase, ligase, protease, amylase, cellulase, pectinase, oxidase, peroxidase, and lipase.

15. The process according to claim 14, wherein said enzyme is a subtilisin protease.

16. The process according to claim 15, wherein said subtilisin protease is subtilisin 309.

17. The process according to claim 16, wherein said subtilisin 309 has been modified in at least position 36.

18. The process according to claim 17, wherein said modification in position 36 is *36D or *36Q.

19. The process according to claim 18, wherein the enzyme has a modification selected from the group consisting of:
*36D, *36D+R170Y+G195E+K251E,
*36D+H120D+R170Y+G195E+K235L,
*36D+H120D+R170Y+G1-
95E+K235L+K251E,
*36D+H120D+G195E+K235L, *36D+N76D,
*36D+N76D+H120D+G195E+K235L, *36Q,
*36D+Q59E+N76-
D+A98R+S99D+H120D+N140D+S141R+-R170Y +G195E+K235L+N248D+T2-55E+L256K+S259D+A272R, and
*36D+Q59E+N76D+A98R+S99D+H 120D+N140D+S141R+S156E +A158-R+A172D+N173K+K235L+N248D+T2-55E+S256K+S259D +A272R.

20. A process for the production of a protease susceptible to inactivation or degradation in a fluid production medium comprising reversibly protecting said protease against inactivation or degradation during the production stage by forming a complex with a polypeptide added to the production medium, wherein the added polypeptide is selected from the group consisting of an antibody and a protease inhibitor, separating the protease from the production medium, deprotecting the protease and recovering the protease product.

21. The process of claim 20, wherein said inhibitor is a protease inhibitor selected from the group consisting of the CI-1, CI-2, PSI, Eglin C, Eglin B, TSI-1, SSI, or VSI inhibitor, variants thereof, and a mixture of many of these.

* * * * *